United States Patent [19]

Fudacz

[11] Patent Number: 5,044,193

[45] Date of Patent: Sep. 3, 1991

[54] LATERAL DISPLACEMENT MEASURING APPARATUS & METHOD

[75] Inventor: Paul M. Fudacz, Chicago, Ill.

[73] Assignee: Dana Corporation, Toledo, Ohio

[21] Appl. No.: 546,493

[22] Filed: Jun. 29, 1990

[51] Int. Cl.$^5$ .............................................. G01N 3/08
[52] U.S. Cl. .................................................... 73/818
[58] Field of Search ................ 73/818, 790, 821, 822, 73/823, 824, 825

[56] References Cited

U.S. PATENT DOCUMENTS

| | | | |
|---|---|---|---|
| 2,173,493 | 9/1939 | Peters | 73/790 |
| 2,471,227 | 5/1949 | Marshall | 374/51 |
| 2,500,068 | 3/1950 | Gerard | 73/790 |
| 2,732,708 | 1/1956 | Linhorst | 374/51 |
| 2,754,675 | 7/1956 | More | 374/51 |
| 2,912,855 | 11/1959 | MacAllister et al. | 73/818 |
| 3,210,993 | 10/1965 | Shoor et al. | 72/768 X |
| 3,550,441 | 12/1970 | Dickinson | 73/818 |
| 3,847,018 | 11/1974 | Aston | 73/818 |
| 3,854,328 | 12/1974 | Schmidt | 73/813 |
| 3,994,157 | 11/1976 | Burk et al. | 73/821 |
| 4,047,425 | 9/1977 | Handy et al. | 73/822 |
| 4,122,704 | 10/1978 | Lutenegger et al. | 73/822 |
| 4,491,021 | 1/1985 | Meline | 73/767 |
| 4,831,738 | 5/1989 | Meline et al. | 33/798 |
| 4,831,882 | 5/1989 | Meline et al. | 73/826 |
| 4,972,719 | 11/1990 | Vinson et al. | 73/790 |

Primary Examiner—Jerry W. Myracle
Attorney, Agent, or Firm—F. B. McDonald

[57] ABSTRACT

A lateral displacement measuring apparatus by which the circumference of an extrudable solid specimen may be continuously measured while the specimen is subjected to compressive forces along an axis. In a preferred form, the apparatus includes a pair of platens, one fixed and one movable, adapted to compressively load the specimen to its functional or performance limit. A first end of a tensile member is coupled to a displacement transducer, the tensile member being in contacting lateral engagement with the specimen, the other end of the tensile member being secured rigidly to an adjustable but fixed support. As the platens are loaded together, thereby squeezing the specimen, the transducer produces a signal corresponding to the magnitude of lateral expansion of the specimen.

11 Claims, 1 Drawing Sheet

LATERAL DISPLACEMENT MEASURING APPARATUS & METHOD

BACKGROUND OF THE INVENTION

This invention relates to systems for determining performance characteristics of extrudable solid materials subjected to compressive forces. More particularly, the invention relates to devices designed to measure lateral expansions of vehicular gaskets for purposes of determining performance or functional limits of such materials.

In continued efforts to find improved materials for use in gaskets, it is necessary to test various proposed materials. One such test involves compression of a material specimen until it begins to extrude laterally. The point at which lateral extrusion becomes significant defines the point at which the material has reached its functional limit for gasketing purposes.

In order to perform lateral extrusion tests, compression platens are typically used in conjunction with mechanical fixtures to provide high compressive forces on test specimens. Such tests are generally performed on circular discs of materials having various specified areas and thicknesses. Generally a specimen is squeezed between two opposed platens, under an increasing compressive force applied by means of a hydraulic ram. As a result, the specimen decreases in thickness over the force cycle. Generally, at some point, the circumference, hence diameter, of the specimen (even of a fibrous material) will begin to increase.

In the past, it has been necessary to monitor the diameter of a test specimen at intervals during the test cycle with either a ruler or calipers. If a specimen had not reached a pre-determined diameter change at a given load, the test was repeated at higher loads until the onset of significant extrusion was realized. This reiterative process continued until the functional limit of the material was ultimately reached. Such trial and error method was not only time consuming, but did not lend itself to modern statistical analyses.

SUMMARY OF THE INVENTION

This invention embodies a test apparatus which can continuously measure lateral extrusion without a series of starts and stops. The apparatus includes the use of a high tensile strength medium, preferably a small diameter wire, which is looped about a test specimen for maintaining continuous physical contact with the specimen as the specimen is extruded under compressive forces. One end of the wire is attached to a linear variable differential transformer (hereinafter referred to as a displacement transducer), while the other end of the wire is attached to a fixed wire end retainer. The retainer is adjustable relative to a platform situated adjacent a pair of platens between which the specimen is compressed. The transducer includes a spring-biased internal core which produces an electrical signal as a function of its movement. The retainer is first positioned to make the wire taut (thus removing all slack) and to "zero" the transducer reading. Upon compression of the specimen between platens, extrusion of the specimen begins, causing the transducer to produce a signal corresponding to the magnitude of the lateral displacement of the wire.

In a preferred form, the apparatus includes the platens, one fixed, the other axially movable along an axis, each platen comprising a load bearing surface generally orthogonal to the axis, one of the surfaces defining a support adapted to retain the specimen. The high tensile strength wire of necessity has a thickness less than the thickness of the specimen.

The method disclosed includes placing the wire about the specimen, adjusting the retainer to make the wire taut, and applying compressive forces to the specimen by means of the platen surfaces to cause the specimen to be compressed. At or near the functional limit of the specimen, the wire becomes further tensioned by lateral expansion of the extrudable specimen, causing the transducer to produce the aforementioned signal corresponding to the amount of lateral displacement.

DETAILED DESCRIPTION OF PREFERRED EMBODIMENTS

Figure 1:
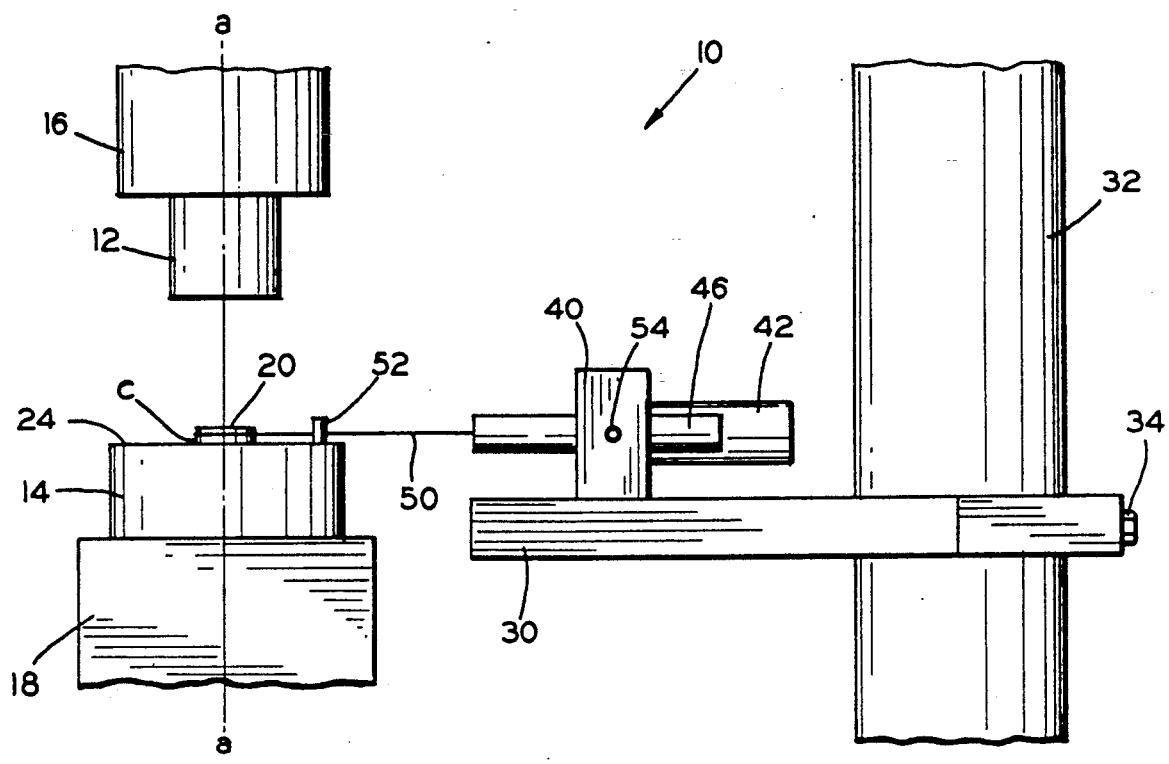
FIG. 1 is a fragmentary view of a lateral displacement measuring apparatus constructed in accordance with a preferred embodiment of the present invention.

Referring to the drawings, a preferred embodiment of the lateral displacement apparatus 10 (FIG. 1) is shown. The apparatus 10 includes an upper platen 12 and a lower platen 14. In this particular embodiment, the upper platen 12 is fixed to a reciprocally movable hydraulic ram 16 and is thus translatable along an axis "a—a" as shown. Conversely, the lower platen 14 is fixed to a stationary base 18, and thus remains relatively immovable.

Figure 2:
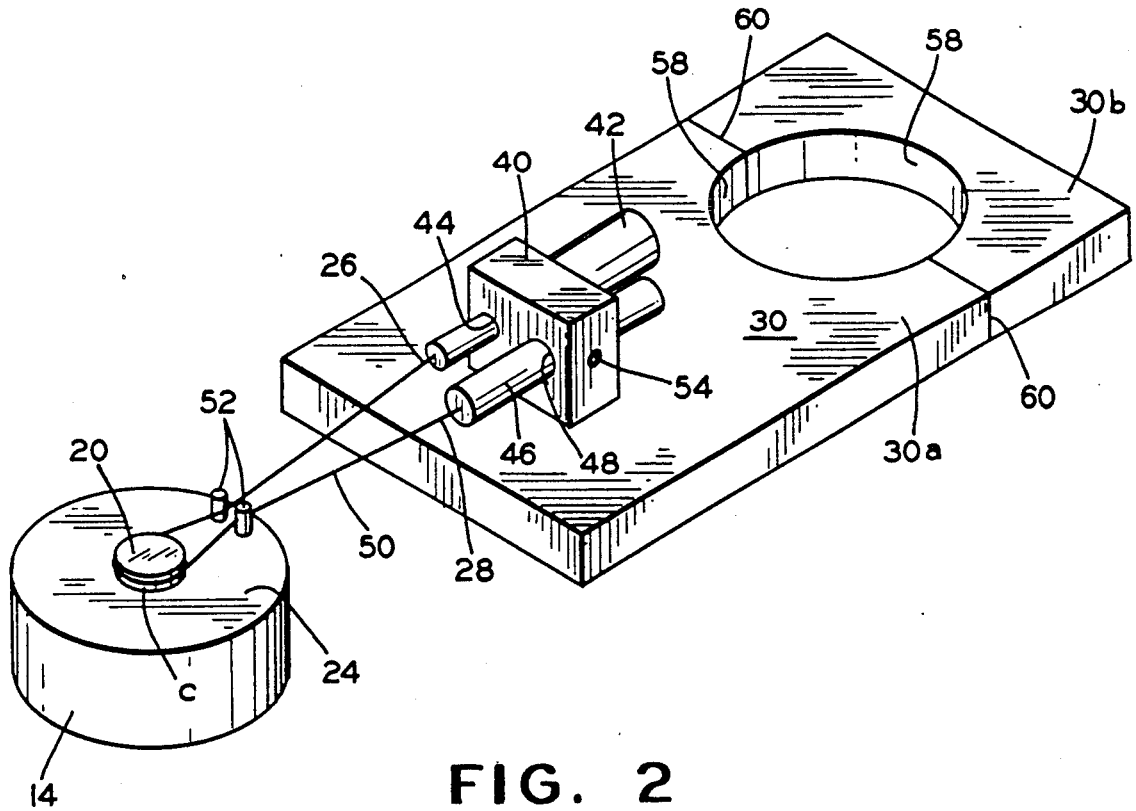
FIG. 2 is an enlarged perspective view of a sub-portion of FIG. 1.

Referring now particularly to FIG. 2, a circular or disc-shaped sample or specimen 20 is placed upon the upper surface 24 of the lower platen 14. A platform 30, formed of two parts, 30a and 30b, is adapted for securement to a cylindrical support 32 (FIG. 1) which is also fixed relative to the base 18. The parts 30a and 30b of the platform 30 are held together by a set of longshaft bolts 34 (FIG. 1). In the preferred embodiment the parts 30a and 30b each provide a semi-cylindrical clamping surface 58 adapted to frictionally engage the cylindrical support 32. The two parts mate together at a break line 60, wherein there may exist a gap, the size of which is defined by the relative coacting sizes of the clamping surfaces 58 and the cylindrical support 32. Although the mounting system of the presently preferred embodiment is as described, other suitable mounting mechanisms may also be utilized.

The platform 30 incorporates an upstanding bracket 40 which contains first and second bores 44 and 48 (FIG. 2). The first bore 44 rigidly supports a displacement transducer 42, which in the preferred embodiment is of the "linear variable differential transformer" type, as will be appreciated by those skilled in this art. The transducer 42 is permanently fixed to the bore 44, and is non-displaceably secured therein. The second bore 48 contains an adjustable wire end retainer 46, defined by a cylinder which is slidable within the bore 48, and which may be secured in any given position by means of a set screw 54. The screw 54 extends transversely with respect to the cylinder 46, in a threaded bore, not shown.

The aforedescribed apparatus accommodates a flexible high tensile strength wire 50, adapted to be looped once about the circular disc 20, shown more clearly in FIG. 2. A pair of wire guide pins 52 are dowled relatively closely together in the upper surface 24 of the lower platen 14 for the purpose of assuring that the amount of wire encircling and contacting the circumference "c" of the disc 20 is maximized.

As earlier noted, whenever a sufficient amount of compressive force is applied to a gasket specimen of extrudable fibrous material, there is a change, i.e. reduction, in the thickness of the specimen accompanied by a slight change in its lateral dimension, hence the specimen tends to bulge laterally. This phenomenon is described by Poisson's Ratio in homogeneous materials in a manner wherein actual measurement of lateral change would be unnecessary, given specific parameters of area, thickness, and material. However, to the extent that head gasket materials consist of nonhomogeneous fibrous facing materials which are often laminated or mechanically clinched to a metallic core, the resulting material characteristics are not subject to simple calculation. In such cases, changes in lateral dimensions must be empirically determined. This invention provides a means for continuously measuring lateral dimensional change of a specimen placed under compression.

A method of employing the above-described apparatus to measure change in lateral displacement is now described. The disc shaped specimen 20 is first placed on the top surface 24 of the lower platen 14. The wire 50 is looped around the circumference of the specimen and between the guide pins 52. The first end 26 of the wire 50 is secured to the transducer 42; the second end 28 of the wire 50 is secured to the adjustable retainer 46. The retainer, as noted earlier, is free to slide within the bore 48. For purposes of set-up, the wire 50 is initially in a slackened or untaut condition by virtue of the position of the adjustment cylinder 46 within the bore 48. Once the wire 50 has been looped around the specimen 20, the upper platen 12 is lowered until the specimen 20 is slightly compressed under a small pre-load. The preload serves to hold the specimen in place while the wire is made taut via adjustment of the retainer 46. The load transducer has an inwardly spring-biased internal core rod (not shown), and care is taken to assure that the taut wire begins to draw the core rod out of the transducer by an amount sufficient to achieve an "electrical zero" position of transducer. At this point the retainer 46 is fixed in place by means of the set screw 54. The test of the specimen is now ready to begin.

Under the preferred procedure, a compressive load is applied by the hydraulic ram 16 at a steady rate. As the diameter of the specimen begins to increase, the wire 50 is placed under additional tension causing the transducer core rod to be drawn from its zero position within the body of the transducer. Displacement of the core rod produces a proportional electrical output, preferably recorded along with the amount of instantaneous force applied. The output of the load tranducer is converted into a visual reading of the magnitude of displacement, and may be displayed either digitally or by an analog device. The preferred method permits the graphing of the relationship between compressive load and lateral displacement, as well as that between load and thickness reduction. To the extent that gasket thickness changes during a compressive force cycle are measured, this invention allows for measurement of instantaneous diameter of a circular test specimen and thus its area. Hence "true stress" versus "true strain" graphs may be generated by use of the apparatus of this invention, based upon instantaneous readings of (a) the specimen surface area, (b) gasket thickness (as measured by distance between platens), and (c) compressive load applied to the specimen.

Referring now back to FIG. 1, it will be appreciated that the guide pins 52 may be accommodated via use of an upper platen 12 which is smaller in diameter than the lower platen 14. This permits positioning of guide pins at the edge of the upper surface 24 of the lower platen 14, and thus which are sufficiently out of the way of the upper platen 12, which must freely engage (i.e. without obstruction) the specimen 20 for application of compressive load.

EXAMPLE

A specimen having a one square inch surface area was employed. The latter was in the shape of a circular disc having a diameter of approximately 29 millimeters (or 1.13 inches). The specimen comprised an aramid fiber on a perforated core, being formed of five to ten percent "Kevlar" fibers. The specimen had fillers in the range of 70-90 percent consisting of inorganic compounds including clay, and binders of 10 to 15 percent consisting primarily of elastomeric compounds. The thickness of the specimen ranged from 0.020-0.100 inch.

The wire 50 had a tensile strength of 350 to 500 thousand pounds per square inch (psi). The wire was formed of steel, having a gage of 10 thousandths of an inch, although a suitable range of wire thickness would be 6 to 15 thousandths. The guide pins were spaced apart a distance equal to approximately one third of the diameter of the specimen.

The force between platens was measured in pounds, with the hydraulic ram 16 capable of producing 100,000 pounds of force. A voltage-load transducer was incorporated which provided an analog reading range of 0 to 10 volts with a linear calibration in pounds up to 100,000 pounds. Thus, one volt translated into 10,000 pounds.

The displacement transducer, used for measurement of change in circumference of the test specimen, had a calibration of one volt equal to 20 thousandths of an inch. Its output ranged in scale up to a total of 10 volts or 200 thousandths of an inch measurement capacity.

Another transducer was utilized to measure distance between mating platen surfaces. The latter incorporated a strain gage extensometer, and was calibrated so that one volt was equal to two thousandths of an inch. Hence, a total of 20 thousandths of an inch displacement was measureable by a ten volt scale.

Finally, the scope of the present invention provides that the gasket specimen compositions may be treated with saturants or liquid coatings, such as either silicone as may be typical in use of aramid fibers, or Teflon in the use of, for example, expanded graphite gasket materials. Where saturants are employed, this invention contemplates the use of heating elements in the platens for purpose of simulating gasket material behavior at the elevated temperatures of their intended use. In such cases, the platen may be heated up to seven or eight hundred degrees Fahrenheit.

Although only one preferred embodiment and method has been detailed and described herein, the following claims envision numerous additional embodiments and methods which fall within their scope.

What is claimed is:

1. An apparatus for measuring lateral expansion of an extrudable solid specimen subjected to compressive forces along an axis; said apparatus comprising:
   (a) a pair of platens relatively movable with respect to one another along said axis, each platen comprising a load bearing surface generally orthogonal to said axis, one of said surfaces defining a specimen support for supporting said specimen;

(b) an elongate flexible high strength tensile member having two ends, wherein an intermediate portion thereof is adapted for being looped about said specimen for making lateral contacting engagement therewith, said tensile member comprising an axial thickness less than the thickness of said specimen; and (c) a reference platform positioned adjacent said support surface, a displacement transducer fixed to said platform, one end of said tensile member being coupled to said transducer, an adjustment means also fixed to said platform, the other end of said tensile member being coupled to said adjustment means; whereby said tensile member may be positioned tautly about said specimen via said adjustment means prior to test of said specimen, so that upon test of said specimen, said specimen is compressed and said tensile member is further tensioned by lateral expansion of said specimen, whereby said displacement transducer produces a signal corresponding to magnitude of said expansion.

2. The apparatus of claim 1 wherein said platform comprises a bracket, said bracket having a bore extending therethrough, said bore containing said adjustment means, said means comprising an adjustable retainer defining a cylinder slidable in said bore, said bracket further containing a second bore parallel to said first bore, said second bore containing said transducer fixed within said second bore.

3. The apparatus of claim 2 wherein said bracket further comprises an adjustment means adapted for axially loosening and fixing the position of said cylinder within said first bore.

4. The apparatus of claim 3 wherein said platform comprises two parts, each defining a clamping surface, each surface adapted to frictionaly engage a support member.

5. The apparatus of claim 4 wherein one of said platens is fixed to an axially movable ram.

6. The apparatus of claim 5 further comprising a pair of guide pins fixed to an edge of said specimen support, said pins positioned intermediately of said specimen and said platform and being spaced apart a distance equal to approximately one third the diameter of said specimen.

7. The apparatus of claim 6 wherein said tensile member comprises a steel wire having a gage thickness in the range of 6 to 15 thousandths of an inch.

8. The apparatus of claim 7 wherein said material specimen is a nonhomogeneous gasket composition.

9. The apparatus of claim 8 wherein said specimen is shaped in the form of a circular disc having a thickness in a range of 0.020 to 0.100 thousandths of an inch.

10. The apparatus of claim 9 wherein said tensile member is a wire formed of steel and having a tensile strength of at least 350 thousand pounds per square inch.

11. The apparatus of claim 10 wherein one of said platens comprises a heating element.

* * * * *